United States Patent [19]

Valehrach

[11] Patent Number: 4,555,028
[45] Date of Patent: Nov. 26, 1985

[54] APPARATUS FOR COMPRESSION TESTING AND SORTING GOLF BALLS

[75] Inventor: Emil M. Valehrach, Phoenix, Ariz.

[73] Assignee: Karsten Solheim, Phoenix, Ariz.

[21] Appl. No.: 605,907

[22] Filed: May 1, 1984

[51] Int. Cl.[4] .......................... B07C 5/34; G01N 3/08
[52] U.S. Cl. .................................. 209/599; 209/605; 73/78; 73/824
[58] Field of Search ..................... 73/78, 818, 824, 52; 209/599, 600, 604, 605, 698

[56] References Cited

U.S. PATENT DOCUMENTS

| | | | |
|---|---|---|---|
| 2,226,600 | 12/1940 | Eddington | 73/78 |
| 2,278,416 | 4/1942 | Atti | 73/818 |
| 2,628,496 | 2/1953 | Wick | 73/818 |
| 3,765,231 | 10/1973 | Erb et al. | 73/824 |
| 3,930,994 | 1/1976 | Conway et al. | 209/698 |

Primary Examiner—S. Leon Bashoe
Assistant Examiner—Andrew J. Anderson
Attorney, Agent, or Firm—Herbert E. Haynes, Jr.

[57] ABSTRACT

An apparatus for testing the compressability of golf balls and sorting them in accordance with predetermined compression ratings. The apparatus includes a golf ball movement path having a rotary anvil on one side thereof for driving the golf balls one at a time through a restricted gap between the anvil and a deflectably biased lever. The gap is sized to be smaller than the diameter of the golf balls so that they will deflect the lever an amount determined by their individual compressability. The amount of lever deflection is sensed and transmitted to an electric circuit which operates a golf ball sorting device that directs the golf balls to different outlets in accordance with their sensed compressability.

40 Claims, 8 Drawing Figures

APPARATUS FOR COMPRESSION TESTING AND SORTING GOLF BALLS

BACKGROUND OF THE INVENTION

1. Field of the Invention

This invention relates generally to mechanisms for testing and classification of articles and more particularly to an apparatus for compression testing golf balls and automatically sorting the golf balls in accordance with adjustably predetermined compression ratings.

2. Description of the Prior Art

As is well known in the golfing art, golf balls vary in resiliency and predetermined levels of resiliency, expressed as a function of compression, have been established for recommended usage purposes. More specifically, a golf ball having a relatively high compression rating is better able to withstand the impact forces applied thereto by a physically strong golfer, such as some men and most male professional golfers. And, golf balls with lesser compression ratings are recommended for use by persons with less physical strength. Golf balls having a high compression rating are considered as being "hard" and are usually identified as having a compression rating of 110 or, simply 100+. Medium hardness golf balls are considered as those having a compression rating of about 100 and are usually identified as having a compression rating of 100. Golf balls which may be considered as being "soft" are those having a compression rating of about 90 and are usually identified as having such a compression rating.

From this it will be seen that some sort of mechanism is needed for establishing the compression rating of golf balls so that they can be properly identified.

One mechanism which can be used for this purpose is a hand operated gage wherein a predetermined spring load is applied to a golf ball which is being held between a spaced pair of flat plates, and the resulting deformation of the ball is indicated on a dial indicator measuring device. This type of hand gage is obviously not suited for use in high volume manufacturing applications.

The only commercially available relatively high volume mechanism known to me is manufactured by the Federal Products Corporation, 1144 Eddy Street, Providence, R.I., and the mechanism is referred to as Model No. 144B-498 golf ball gage. Briefly, this mechanism includes a hopper for containing a plurality of golf balls which are serially fed to a measuring station. The measuring station includes an anvil upon which the golf balls to be tested come to rest. An elongated weighted lever arm is pivotably moved so as to apply a deadweight load, and thus compress the golf ball between the anvil and the extending end of the lever arm. An electronic system is used to convert the travel of the lever arm into a voltage signal, and amplify the signal and direct it to an electronic classifier which compares the value of the received signal with adjustably predetermined values. The classifier provides an appropriate visual indication of the test results, i.e., colored lights, and, in cooperation with a rotary timing device, sequences the release of the measurement signals for operation of an appropriate one of a plurality of disposal solenoids. Tested golf balls are pushed out of the measuring station into a disposal chute which includes trap doors that are operated by the disposal solenoids. Balls falling into different levels of the compression rating system are classified by being either allowed to pass directly through the disposal chute or are diverted by the appropriately operated trap door. In order to achieve acceptable production levels in this prior art mechanism, two separate measuring stations of the type described above are provided and a golf ball shuttling device is provided to alternately direct golf balls first to one station and then to the other. And, of course, each measuring station is complete with the necessary duplication of operational elements such as the anvil, weighted lever arm, and the like. The two measuring stations are operated 180° out of phase with each other so as to speed up the overall production capability of the mechanism.

This prior art mechanism is a very large and expensive mechanism and is extremely complex both from mechanical and electronic standpoints. And, in addition, even with the continuously and alternately operating dual measuring stations, the measuring and sorting accuracy is not guaranteed at speeds above 3200 golf balls per hour. Further, since a golf ball is at rest during the measuring operation, the compression force exerted thereon is applied along a single diameter of the ball, and the resulting compression value may, or may not, be indicative of an average compression value, such as would result from applying the compression forces along several diameters of the ball being tested.

Therefore, a need exists for a new and improved apparatus for testing the compression and sorting golf balls which overcomes some of the problems and shortcomings of the prior art.

SUMMARY OF THE INVENTION

In accordance with the present invention, a new and improved apparatus for compression testing and sorting of golf balls is disclosed. The apparatus includes a suitable hopper which supplies golf balls one at a time to a compression measuring device wherein the golf balls are driven through a restricted gap of predetermined size. The golf ball driving is accomplished by a rotary anvil which also serves as a bearing surface that defines a fixed side of the restricted gap against which the ball being tested bears during its movement through the restricted gap. The other side of the restricted gap is defined by a spring-loaded compression lever which is deflected a distance which is indicative of the compressibility, or hardness, of the golf ball being tested. The amount of deflected movement of the compression lever is sensed by a deflection sensing means that is operatively coupled to an electric circuit for selectively applying electric power to relaying circuitry for operation of a golf ball sorting means. After a golf ball is driven through the restricted gap, it moves into the golf ball sorting means which selectively directs the golf ball to one of three outlets in accordance with the result of the compression test accomplished on that ball.

From the above, it will be appreciated that the apparatus of the present invention is relatively simple in comparison to the hereinbefore described prior art mechanism. The substantially reduced complexity of the present apparatus results in less initial cost, set-up time, and maintenance. It will further be appreciated that since the golf balls being tested are driven through the compression measuring device, and do not have to be brought to an atrest position, as was the case in the prior art machine, the production rate of the apparatus of this invention is considerably higher than that of the prior art. The single measuring station of the present invention has a higher production rate than the combined production rates of the prior art dual station mechanism.

The driven movement of the golf balls that are being tested provides an additional advantage of the present invention. When being driven, a golf ball will roll through the restricted gap between the rotating anvil and the compression lever. Therefore, the compression testing will be taken along various diameters of the ball with the result being a highly reliable average reading of the golf ball rather than one taken on a single diameter.

Accordingly, it is an object of the present invention to provide a new and improved apparatus for compression testing and sorting of golf balls.

Another object of the present invention is to provide a new and improved apparatus for compression testing and sorting of golf balls which is inexpensive to manufacture and is simple to use.

Another object of the present invention is to provide a new and improved apparatus for compression testing and sorting of golf balls wherein the golf balls being tested are uninterruptedly moved through the apparatus for high production purposes.

Another object of the present invention is to provide an apparatus of the above described character wherein the uninterrupted driving movement of the golf balls results in a rolling thereof during testing of the compression so that the compression rating will be an average of the readings taken on a plurality of diameters.

Another object of the present invention is to provide an apparatus of the above described type wherein golf balls are drivingly moved through a restricted gap which is yieldably expandable in accordance with the hardness of a particular golf ball being tested, with the amount of the expansion being sensed by a deflection sensing means which is coupled to control the operation of an electric circuit which, in turn, operates a sorting means that directs the tested golf balls to various outlets in accordance with their compression ratings.

The foregoing and other objects of the present invention as well as the invention itself, may be more fully understood from the following description when read in conjunction with the accompanying drawings.

DESCRIPTION OF THE PREFERRED EMBODIMENT

Figure 1:
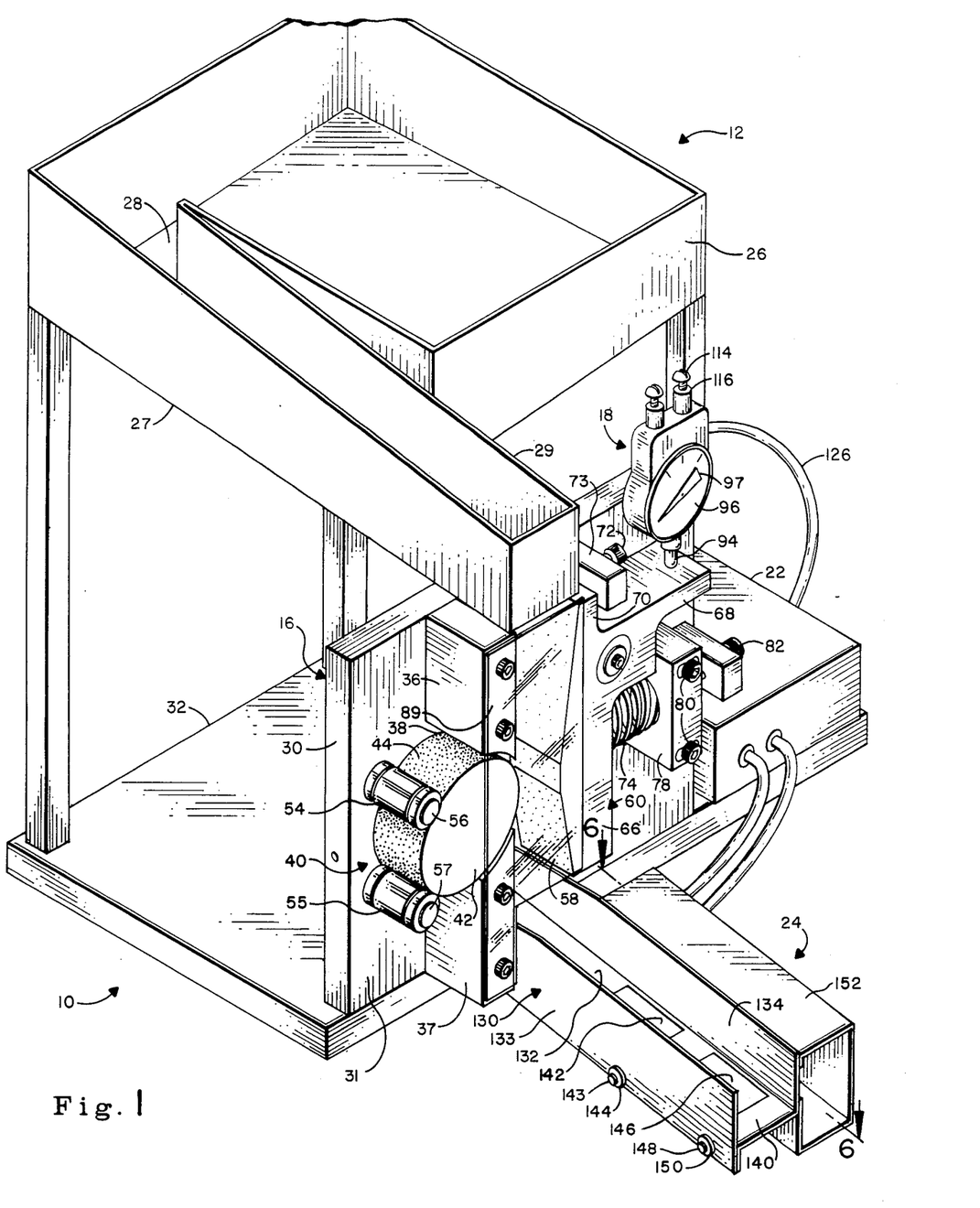
FIG. 1 is a perspective view of the apparatus of the present invention for compression testing and sorting of golf balls.

Referring more particularly to the drawings, FIG. 1 shows the apparatus of the present invention for compression testing and sorting golf balls which is indicated in its entirety by the reference numeral 10. As will hereinafter be described in detail, the apparatus 10 includes the major components of a hopper 12 for delivering golf balls 14 (one shown in FIG. 2) to a compression measuring device 16. A sensing means 18 is provided for sensing the output of the measuring device 16 and responding by controlling the operation of an electric circuit 20 (shown in FIG. 8) which is contained, for the most part, within the circuit box 22 shown in FIG. 1. The electric circuit 20 is employed for operation of a golf ball sorting means 24.

The hopper 12 is shown as including an upwardly opening box-like structure 26 having a delivery chute 27 through which golf balls to be tested are delivered to the measuring device 16. Accordingly, the delivery chute 27 has an input end 28 proximate the box-like structure 26 into which the golf balls will move, and having an outlet end 29. Hoppers of this general type are well known in the art and can include such devices as vibrators (not shown) to prevent article jamming within the box-like structure 26 and flow control devices (not shown) within the chute 27 for insuring controlled, one at a time exiting of the articles therefrom. In all such devices, the prime mover is gravity. Therefore, the hopper 12 will supply golf balls one at a time to the compression measuring device 16 and the golf balls will fall under the influence of gravity from the outlet end 29 of the chute 27 into the measuring device 16.

Figure 2:
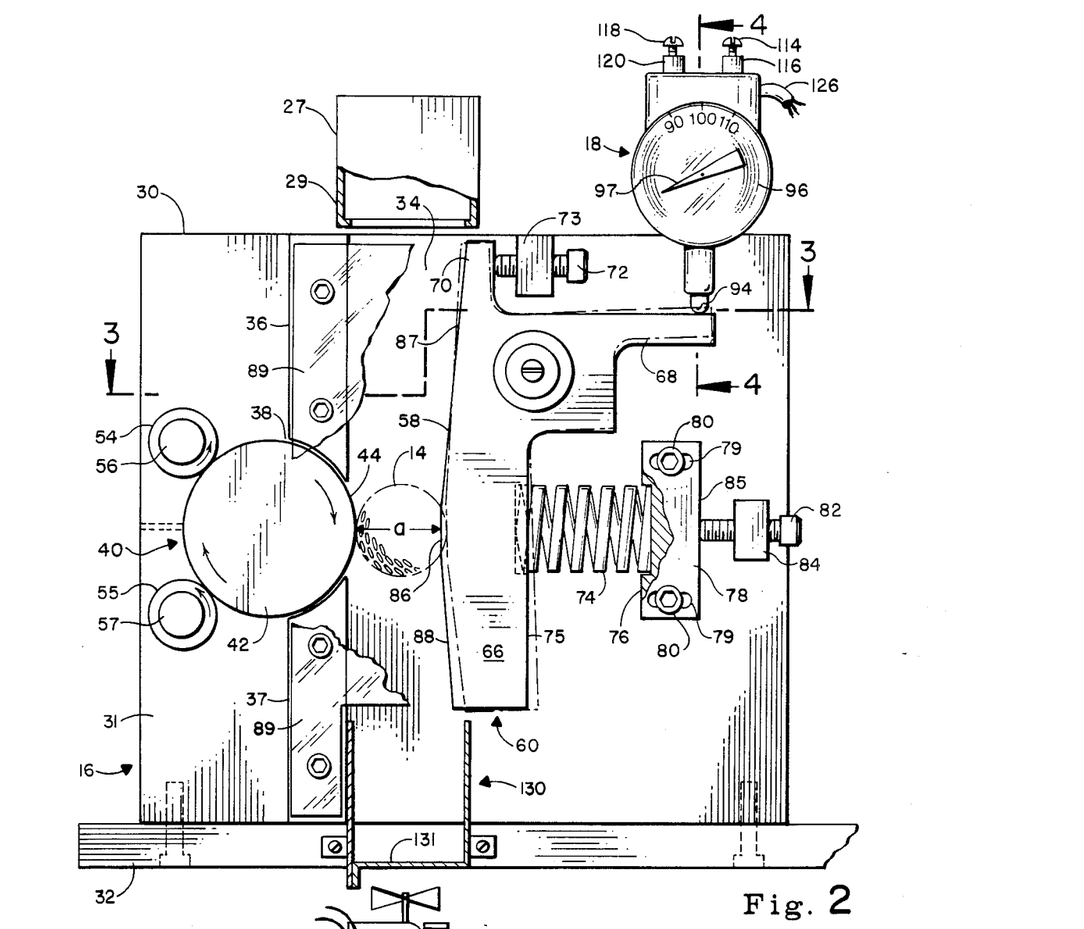
FIG. 2 is a front elevational view of the compression testing portion of the apparatus of the present invention.

As seen best in FIG. 2, the compression testing device 16 includes a plate 30 having a planar face surface 31, with the plate 30 being suitably mounted on a base 32, so as to be disposed in a vertical attitude. The structural and functional elements which are now to be described are mounted on the plate 30 so as to define a vertical golf ball movement path 34 which is open at the top for receiving golf balls from the outlet end 29 of the hopper chute 27, and is open at the bottom for directing the golf balls to the sorting means 24, as will hereinafter be described in detail.

An upper guide bar 36 and a lower guide bar 37 are mounted on the face 31 of the plate 30 in vertical alignment with each other and are spaced apart to provide a transverse opening 38 therebetween. A rotary anvil 40 including a cylindrical drum 42 is mounted proximate the opening 38 formed between the guide bars 36 and 37 so that a portion of the drum 42 is located in the opening 38 and the peripheral surface 44 of the drum extends into the golf ball movement path 34 for reasons which will become apparent as this description progresses.

Figure 3:
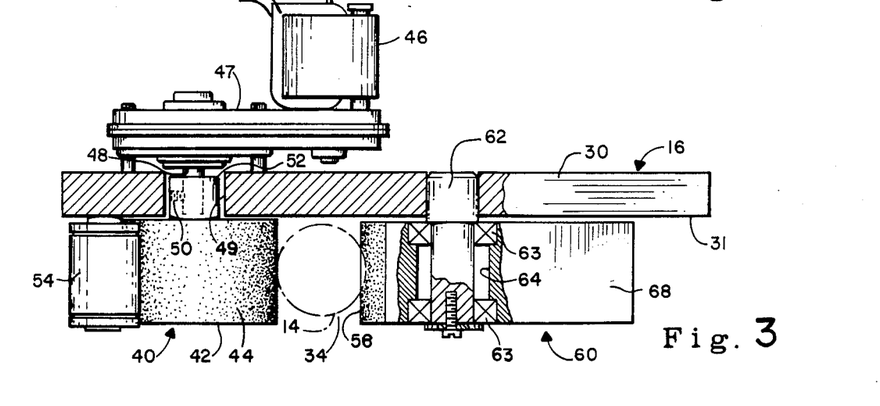
FIG. 3 is a sectional view taken along line 3—3 of FIG. 2.

FIG. 3 shows a suitable variable speed motor 46 having a reduction gear box 47 which is mounted on the back side of the plate 30. The output shaft 48 of the gear box 47 extends into an opening 49 formed through the plate 30 and the output shaft 48 is secured, such as by a set screw 50, in a bore provided in a boss 52 which extends integrally and axially from the drum 42 of the rotary anvil 40.

A spaced pair of rollers 54 and 55 are rotatably journaled on suitable shafts 56 and 57, respectively, which are fixedly mounted so as to extend normally from the face 31 of the plate 30. The rollers are disposed to be in bearing engagement with the peripheral surface 44 of the drum 42 of the rotary anvil 40 to support the anvil against thrust forces exerted thereon in golf ball compression testing operations.

From the above, it will be seen that the upper and lower guide bars 36 and 37 and the rotary anvil 40 define one side, the lefthand side in FIG. 2, of the golf ball movement path 34.

The opposite side of the golf ball movement path 34 is defined by an elongated bearing surface 58 of a compression lever 60 which, in the preferred embodiment, is in the general form of a bell crank lever. The lever is pivotably rotatable about an axis defined by a shaft 62 which is fixedly carried in the plate 30 so as to extend normally from the face 31 thereof and the bell crank lever 60 is journaled for free rotation about the stub shaft on suitable bearings 63 which are carried in a bore 64 formed at the fulcrum, or elbow, of the lever. The bell crank lever 60 is disposed so that one of its arms 66, hereinafter referred to as the load arm, depends from the fulcrum of the lever and the load arm 66 has the elongated bearing surface 58 formed on one side thereof. The other arm 68 extends substantially horizontally from the fulcrum of the lever in a direction away from the golf ball movement path 34, and this other arm 68 will hereinafter by referred to as the movement transmitting arm. The bell crank compression lever 60 has an ear 70 extending upwardly from the fulcrum thereof. The ear 70 is normally in bearing engagement with an adjustable stop screw 72 that is threadingly carried in a boss 73 fixedly mounted on the face 31 of the plate 30.

A compression spring 74 is mounted so that one of its ends is in a suitable pocket formed in the side surface 75 of the load arm 66 of the lever 60, with the surface 75 being opposite to the bearing surface 58 of the lever. The other end of the compression spring is contained in a pocket provided on one side surface 76 of a block 78. The block 78 is provided with elongated openings 79 and suitable cap screws 80 pass through the openings 79 for threaded attachment to the plate 30. By virtue of the elongated openings 79, the block 78 can be adjustably moved toward or away from the load arm 66 of the lever 60 so as to adjust the biasing load applied by the spring 74 on the lever. In that the block 78 is under a load due to the spring 74, a position adjusting screw 82 is threadingly carried in a boss 84 provided on the face 31 of the plate 30 so as to bear agains the opposite side 85 of the block. Thus, with the cap screws 80 loosened, the positioning screw 82 is employed to precisely control the spring adjustment positioning of the block 78.

The compression spring 74 therefore biasingly urges the bell crank lever 60 for pivotable movement in a clockwise direction about its fulcrum as viewed in FIG. 2. However, the upstanding ear 70 in conjunction with the adjustable stop screw 72 prevents such clockwise pivotable movement of the bell crank lever. Thus, the compression spring 74 is employed to provide a resistance to counterclockwise pivotable movement of the lever resulting from compression testing of the golf balls as will hereinafter be described in detail.

The elongated bearing surface 58 provided on the compression lever 60 has a flat 86 provided thereon which is positioned so as to be in laterally spaced alignment with the rotational axis of the rotary anvil 40 and to provide a gap a between the periphery 44 of the drum 42 and the flat 86. The bearing surface 58 is further provided with an upper portion 87 which slopes away from the flat 86 to provide a guiding surface for incoming golf balls and a lower portion 88 which also slopes away from the flat to provide relief clearance for the golf balls emerging from the flow path. The back surface of the golf ball flow path is defined by the face 31 of the plate 30 and the front of the golf ball movement path is closed by a plate 89, preferably transparent, which is mounted so as to extend in cantilever fashion from the upper and lower guide blocks 36 and 37, respectively.

As indicated by the golf ball 14 shown in the gap a, the gap is set by positioning of the stop screw 72, so as to be smaller than the diameter of the golf ball and thus form a restriction in the flow path 34. A golf ball falling into the flow path 34 will be frictionally gripped by the rotary anvil 40 and the bearing surface 58 of the lever 60. Both the periphery 44 of the drum 42 and the bearing surface 58 have roughened high-friction finishes thereon, such as is provided on sand paper, crocus cloth, and the like, as indicated by the stipple shading in FIG. 3, to insure positive gripping of the golf ball 14. When gripped in this manner, the rotary anvl 40 will drive the golf ball 14 through the restricted gap a which causes pivotable movement of the compression lever 60 from its normal solid line position shown in FIG. 2 to a dash line position shown in the same figure. The amount of resistance to the pivotable deflection of the lever 60 is a function of the adjustable load placed thereon by the compression spring 74, and the amount of compression loading on the golf ball 14 as it is driven through the restricted gap a is determined by the size of the golf ball 14 in comparison to the size of the restricted gap a. Both the resistance to pivotable deflection and the size of the restricted gap a are adjustable as hereinbefore described and thus can be set to suit the desired requirements.

The following examples of the above described adjustable settings have been tested and found to be satisfactory and are presented herein for completeness of the disclosure and are not intended as a limitation of the present invention. Assuming that the golf balls being tested have an average diameter of 1.680 inches, a gap a setting of about 1.565 inches will result in a restriction of about 0.115 inches. The compression spring 74 is adjusted to exert between 210 and 215 pounds for a 3/16 inch compression. These settings result in compression ratings which correspond to those obtained by using the spaced flat plates of the hereinbefore discussed hand gage.

From the above, it will be seen that in order for a golf ball to be driven through the restricted gap a, the golf ball will be deformed from its normal spherical shape, i.e., flattened. A hard golf ball will be flattened less than a softer golf ball and therefore a hard golf ball will cause a larger pivot deflection of the compression lever 60 in comparison to a softer golf ball.

In that the compression lever 60 is preferably of a bell crank configuration, movement of the load arm 66 thereof as described above, will be accurately reproduced by movement in another direction by the movement transmitting arm 68. It will be noted that the distance between the pivot axis, defined by the stub shaft 62, and the flat 86 is substantially the same as the distance from the axis to a point on the movement transmitting arm 68 which is in engagement with the movement sensing means 18. Therefore, the deflected movement of the load arm 66 taken at the flat 86 thereof will be substantially equal, i.e., a ratio of 1:1, to the movement imposed on the sensing means 18. This ratio could, of course, be altered if desired such as, for example, by lengthening the distance from the rotational axis to the point of contact of the movement transmitting arm 68 with the sensing means 18 which, of course, would result in larger, or amplified, movements being imposed on the sensing means 18.

The compression lever 60 is preferably of the above described bell crank configuration. However, it will be appreciated that this bell crank configuration is not necessary for operation of the present invention. For example, a simple lever (not shown) having arms extending oppositely from its pivot axis could be used with the deflection forces being applied on the arm on one side of its pivot axis and the sensing means 18 being positioned to sense movement on the other arm on the opposite side of the pivot axis.

Figures 4, 5:
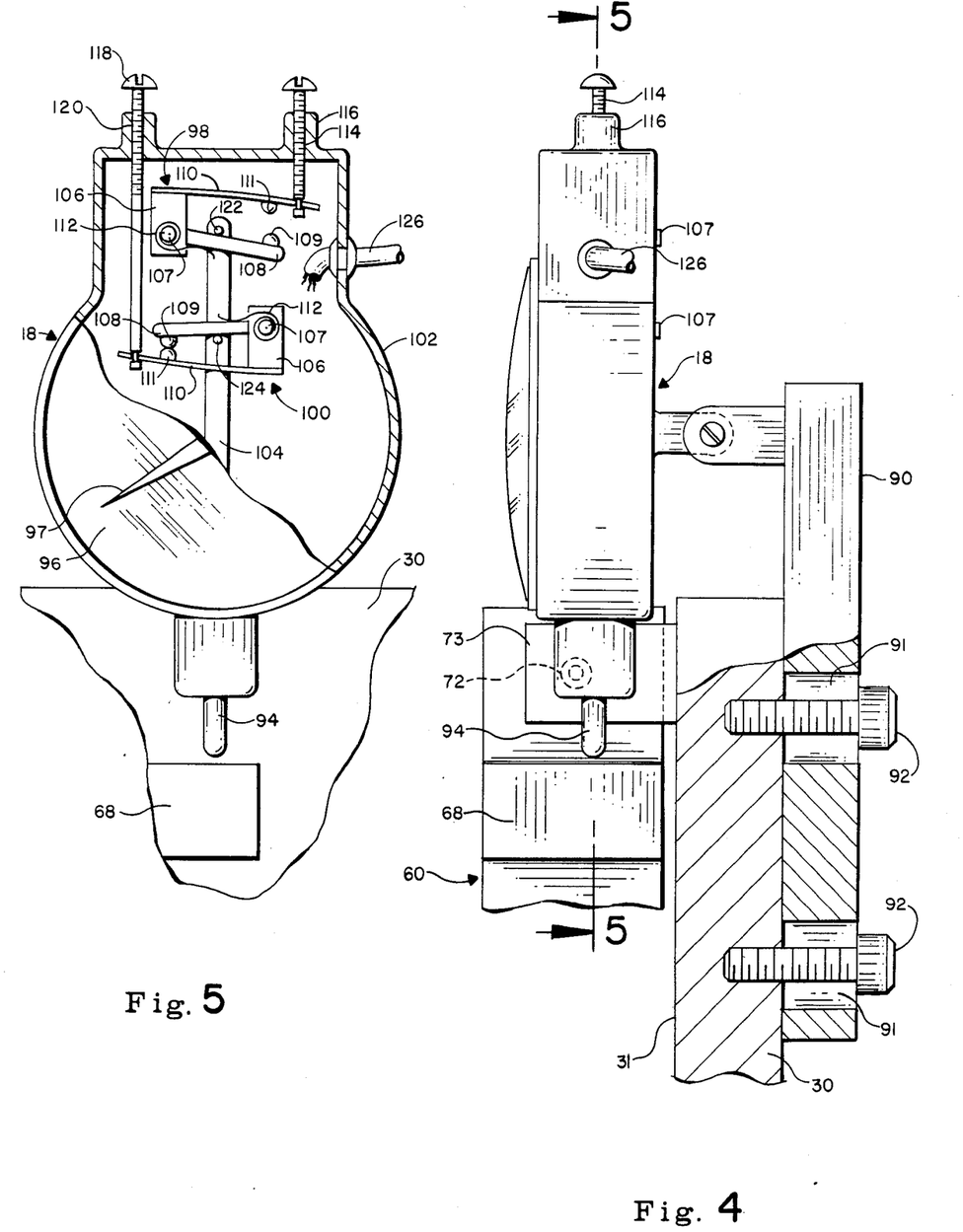
FIG. 4 is an enlarged fragmentary sectional view taken along the line 4—4 of FIG. 2.
FIG. 5 is a fragmentary sectional view taken along the line 5—5 of FIG. 4.

In any case, the movement sensing means 18 is mounted on the plate 30 so as to sense movement of the compression lever 60 and respond by controlling the operation of the electric circuit 20 as hereinbefore mentioned. The sensing means 18, as seen best in FIGS. 4 and 5, is mounted on a bracket 90 having a spaced pair of elongated holes 91 through which suitable cap screws 92 pass for threaded engagement in internally threaded bores provided in the plate 30. Due to the elongated holes 91, the bracket 90, and thus the sensing means 18 carried thereon, can be vertically adjusted for proper positioning relative to the movement transmitting arm 68 of the compression lever 60.

The preferred sensing means 18 is a commercially available product which is a special mechanism of the type commonly referred to as a dial indicator. The product is available from the Federal Products Corporation, 1144 Eddy Street, Providence, R.I., 02901, and is identified as product No. 134B8-R1 D9. Briefly, the sensing means 18 has the usual components of a conventional dial indicator including a plunger 94 for sensing movements and providing a visual indication of the amount of such movement on a dial 96 having a rotating hand 97. Since dial indicators are well known it is deemed unnecessary to show and describe the internal mechanisms of the dial indicator which respond to plunger movement by rotatingly moving the hand 97. The difference between a conventional dial indicator and the one employed in the present invention is that the sensing means 18, or special dial indicator, is provided with a pair of adjustable switches 98 and 100, that are mounted in the indicator housing 102 and are operated by linear movements of the internal portion 104 of the plunger 94 as will now be described.

The switches 98 and 100 are identical structures, thus, the following description of the switch 98 will be understood to also apply to the switch 100. The switch 98 is provided with a plate structure 106 which is carried on a shaft 107 which is fixed in the housing 102. A rigid switch arm 108 having a suitable contact 109 on its extending end, is pivotably mounted on the shaft 107 and a flexible switch arm 110 having a contact 111, is carried on the plate structure 106 in spaced apart relationship with the pivotably movable rigid switch arm 108. A coil spring 112 is concentrically wound on the shaft 107 with its internal end being attached to the shaft in a conventional well known manner and having its extending end in bearing engagement with the pivotable rigid switch arm 108 to bias it towards the flexible arm 110. An adjustment screw 114 is threadingly carried in a suitable boss 116 provided on the indicator housing 102 with the internal end of the adjustment screw 114 being attached to the extending end of the flexible switch arm 110. Threaded movement of the adjusting screw 114 will flexibly move the switch arm 110 toward or away from the pivotably movable switch arm 108 for adjusting the amount of pivotable movement of the switch arm 108 that will be required to open and close the switch 98. A similar, but longer adjustment screw 118 is mounted in the boss 120 and is attached to the extending end of the flexible switch arm 110 of the switch 100 and operates for adjusting the switch 100 in the same manner as described above.

The internal portion 104 of the plunger 94 has a first laterally extending pin 122 which is in engagement with the upper surface of the pivotably movable switch arm 108 of the switch 98. A second laterally extending pin 124 is provided on the internal portion 104 of the plunger 94 with this second pin being disposed so as to be below the lower surface of the pivotably movable switch arm 108 of the switch 100. The plunger 94 is shown in its normally extended position and is thus at its extended limit. In this position, the lower switch 100 will be closed as shown by virtue of its spring 112. Upward movement of the plunger 94 in response to pivotable movement of the compression lever 60 will pivotably move the switch arm 108 of the switch 100 out of contact with the flexible switch arm 110, after a predetermined amount of travel of the plunger 94, as determined by the above described adjusting features, and will thus open the switch 100 after a predetermined amount of pivot movement of the compression lever 60. This same normally extended position of the plunger 94 will, by virtue of the first pin 122, hold the switch 98 open, and after a predetermined and adjustably variable amount of movement of the lever arm 60 will allow the switch 98 to close.

From the above, it will be seen that the switch 100 will open when the compression of a particular golf ball being tested is above an adjustably predetermined value. Similarly, the top switch will close when a particular ball being tested has a compression rating above an adjustably predetermined value. And, when the bottom switch 100 is opened and the top switch 98 has not been moved to its closed position, i.e., both switches are open, the particular golf ball being tested has a compression rating which is between the lower rating which opens the bottom switch 100 and the higher rating which closes the top switch 98.

The switches 98 and 100 are coupled by a suitable wiring cable 126 to the circuit box 22, and are employed to control the operation of the electric circuit 20 as will hereinafter be described.

Before describing the electric circuit 20, the operation and preferred structural details of the golf ball sorting means 24 will be described to facilitate understanding of the reasons behind the functions of the electric circuit 20.

Figure 6:
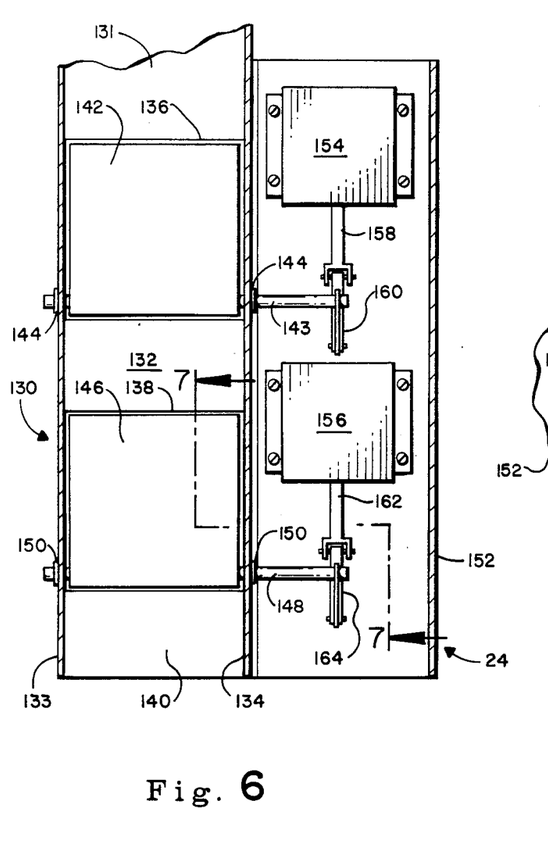
FIG. 6 is an enlarged fragmentary sectional view taken along the line 6—6 of FIG. 1.
Figure 7:
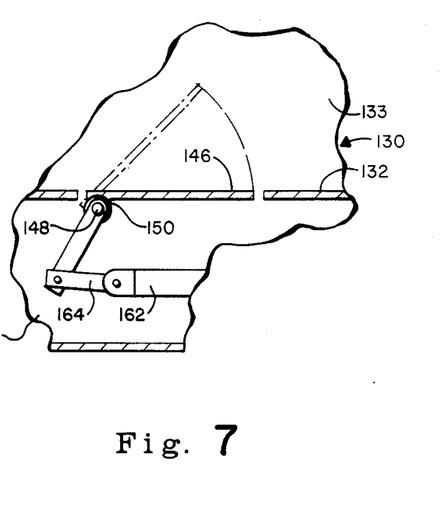
FIG. 7 is a fragmentary sectional view taken along the line 7—7 of FIG. 6.

As shown in FIGS. 1, 6 and 7, the golf ball sorting means 24 includes a chute 130 having an inlet end 131 for receiving golf balls from the compression measuring means 16. The chute 130 is of upwardly opening U-shape in cross section to provide a floor 132 with spaced apart upstanding sidewalls 133 and 134. The inlet end 131 of the chute 130 is connected to the plate 30 in any suitable manner such as that shown in FIG. 2, and is elevated so that the received golf balls will roll down the chute under the influence of gravity. A first outlet opening 136 is formed through the floor 132 proximate the inlet end 131 of the chute and a second outlet opening 138 is provided in spaced downstream relationship with the first outlet opening 136. As will become apparent as this description progresses, the chute 130 is provided with the above mentioned first and second outlet openings 136 and 138, and a third outlet opening 140 is provided at the extending end of the chute and the golf balls are automatically directed through the proper one of those outlet openings in accordance with their compression ratings.

The first outlet opening 136 provided in the floor 132 of the chute 130 is provided with a hatch, or trap door 142 which is fixedly attached to a cross shaft 143. The shaft 143 is rotatably journaled in suitable bushings 144 provided in the depending lower edges of the opposite sidewalls 133 and 134 of the chute in the manner best seen in FIG. 7. The second outlet opening 138 provided in the floor 132 is also provided with a hatch, or trap door 146 which is attached to a shaft 148 that is rotatably journaled in the suitable bushings 150. The shafts 143 and 148 both extend beyond the sidewall 134 of the chute into an elongated housing 152 which is attached in any suitable manner to the sidewall 134 of the chute 130 and is thus supported thereby.

The housing 152 is provided to enclose a first solenoid 154 and a second solenoid 156. The first solenoid is provided with the usual armature rod 158 which is movable between an extended position and a retracted position in the manner well known in the art. The extending end of the armature rod 158 is coupled by a linkage assembly 160 for rotational driving of the shaft 143 and thus movement of the trap door 142 between a first position of closing the first outlet opening 136 and a second position of opening that outlet opening 136. The second solenoid 156 has its armature rod 162 coupled by means of a suitable linkage arrangement 164 for rotating the shaft 148 to move the trap door 146 between its first position of closing the second opening 138, as shown in solid lines in FIG. 7, and a second position of opening that second opening 138 as shown in dashed lines in that same figure.

As shown in FIG. 6, the trap door 142 mounted in the first outlet opening 136 is in its closed position when the armature rod 158 of the solenoid 154 is extended. And, similarly, the trap door 146 mounted in the second outlet opening 138 is in its closed position when the armature rod 162 of the solenoid 156 is in its extended position. Both of the solenoids 154 and 156 have their respective armature rods in the illustrated extended positions when the solenoids are deenergized.

Figure 8:
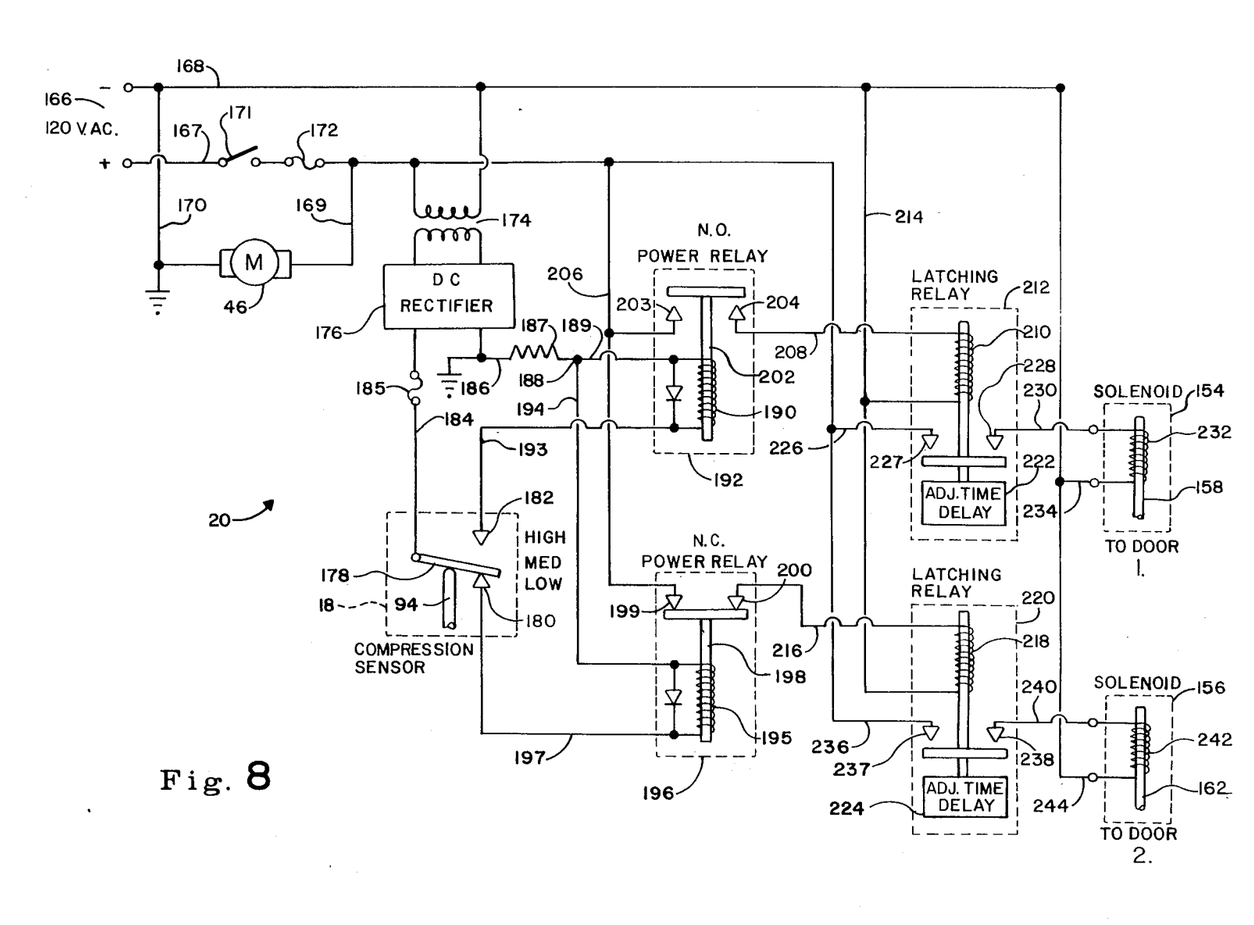
FIG. 8 is a schematic diagram of the electric circuit of the apparatus of the present invention.

The electric circuit 20, as seen in FIG. 8, is provided with means 166 for connection thereof to a suitable source of electric power such as a standard 120 V AC outlet (not shown). The hereinbefore described motor 46 which drives the rotating anvil 40 is connected across the positive voltage line 164 and the negative, or ground line 168 by conductors 169 and 170, respectively. The high voltage line 167 is provided with a suitable on/off switch 171 and a fuse 172. A step-down transformer 174 is employed to produce a reduced value voltage and the transformer is connected to a rectifier 176 for changing the reduced voltage from AC to DC for operation of certain parts of the circuit 20 as will be seen as this description progresses.

The electrical components of the hereinbefore described sensing means 18 are shown schematically as including a pivot contact 178 which is moved by the plunger 94 of the sensing means 18. The contact 180 schematically represents the switch 100 (FIG. 5) and the contact 182 schematically represents the switch 98 of the sensing means 18.

The first conductor 184 extending from the DC rectifier 176 has a suitable fuse 185 therein and is connected to the pivot contact 178 of the sensing means. The second conductor 186 extending from the DC rectifier has a resistor 187 therein and is grounded as indicated, and extends to a junction 188. A conductor 189 couples the junction 188 to one end of the coil 190 of a normally open power relay 192 with the other end of the coil 190 being connected by means of a conductor 193 to the contact 182 of the sensing means 18. A conductor 194 also extends from the junction 188 to one end of the coil 195 of a normally closed power relay 196. The opposite end of the coil 195 is connected by the conductor 197 to the other contact 180 of the sensing means 18.

When the sensing means 18 senses a low compression ball, as hereinbefore fully described, the pivot contact 178 will be in engagement with the contact 180, which represents the low compression position of the sensing means 18. When the on/off switch 171 is closed and the sensing means is in the low compression position, power will be supplied to the coil 195 of the normally closed power relay 196, thus energizing that relay 196 to move its armature rod 198 out of engagement with its two contacts 199 and 200, i.e., will energize that relay from its normally closed position to its open position.

When the sensing means senses a medium compression ball, the pivot contact 178 will be moved out of engagement with the contact 180 into an intermediate position wherein the pivot contact 178 is not in engagement with either of the contacts 180 or 182. In this medium compression position of the sensing means 18, the power relay 196 will be in its normally closed position, and the power relay 192 will be in its normally open position.

When the sensing means 18 senses a high compression golf ball, the pivot contact 178 will be moved into engagement with the contact 182 which represents the high compression position of the sensing means 8. When in this high position, the circuit to the normally open power relay 192 will be completed to pull its armature rod 202 into contact with its two contacts 203 and 204. In other words, when the sensing means 18 senses a high compression ball, the normally open power relay 192 will be energized to move it to its closed position.

A conductor 206 is connected to the high voltage AC power line 167 to supply power to the contact 203 of the normally open relay 192 and to the contact 199 of the normally closed relay 196.

The contact 204 of the normally open relay 192 is connected by a conductor 208 to one end of the coil 210 of a first latching relay 212, the other end of which is connected to ground line 168 by a conductor 214. Similarly, the contact 200 of the normally closed power relay 196 is connected by a conductor 216 to one end of the coil 218 of a second latching relay 220 with the other end of the coil 218 being connected to ground through the conductors 214 and 168.

Both of the latching relays 212 and 220 are normally open and when energized will move to their closed positions and maintain those closed positions for predetermined lengths of time. Since the motor 46 is a variable speed motor as hereinbefore mentioned, the golf ball testing speed of the apparatus 10 may be varied to suit desired output rates. For this reason, the latching times of the relays 212 and 220 are preferably adjustable so that, as will become apparent as this description progresses, the trap doors 142 and 146 will be held open for lengths of time that are suitable for the output rate of the apparatus 10.

Latching relays having means for adjusting the delay times are well known in the art, therefore, the adjustable timing devices associated with the latching relays 212 and 220 are indicated in block form at 222 in conjunction with the relay 212 and at 224 in conjunction with relay 220. Such adjustably variable latching relays are commercially available at virtually any well supplied electric parts house, with an example of such a relay being identified as a time delay relay, class 9050, type A01D, manufactured by the Square D Corp.

The first latching relay 212, when energized, will supply high voltage AC from the power line 167 through conductor 226, contacts 227 and 228, and through conductor 230 to one side of the coil 232 of the first solenoid 154 of the golf ball sorting means 24. The opposite side of the coil 232 is connected by a conductor 234 to the ground line 168. Similarly, the second latching relay 220, when energized, will supply high voltage AC from the power line 167 through conductor 236, contacts 237 and 238, and through the conductor 240 to one side of the coil 242 of the second solenoid 156. The opposite side of the coil 242 is connected to a ground through conductors 244 and 168.

OPERATION

When the apparatus 10 is to be operated, the on/off switch 171 will be closed to operate the rotary anvil 40 and to apply power to the electric circuit 20 in the manner fully described above. To insure a complete understanding of the operation of the apparatus 10 in general, and the electric circuit 20 and golf ball sorting means 24 in particular, a description of the various operational modes, or cycles, will now be presented.

The first operational mode may be referred to as the "soft" golf ball mode wherein the golf ball being tested has a compression rating which is not high enough to move the plunger 94 of the sensing means 18 a sufficient distance to move the pivot lever 178 out of engagement with the contact 180, in other words, the switch 100 (FIG. 5) is closed. When this condition exists, the circuit to the normally open power relay 192 will be open so as not to energize the latching relay 212 or the first solenoid 154. The solenoid 154 is a normally extended device as hereinbefore mentioned, thus, the first trap door 142 will be closed. In this same "soft" golf ball operational mode, the circuit to the normally closed power relay 196 will be completed thus energizing that relay to move it to its open position. When open, the power relay 196 opens the circuit to the latching relay 220 and this, in turn, opens the circuit to the second solenoid 156. Since the solenoid 156 is also a normally extended device, the second trap door 146 will also be closed. Therefore, tested golf balls having a compression rating below the adjustably preset low, or "soft" compression rating, will drop from the measuring device 16 into the chute 130 and will exit the chute through the third outlet opening 140 provided at the extending end thereof.

The second operational mode is herein referred to as the "medium" golf ball mode wherein the golf ball being tested has a compression rating which moves the pivot contact 178 into the intermediate position between the contacts 180 and 182, of the compression sensing means 18. In other words, both switches 98 and 100 (FIG. 5) will be open. In this medium operational mode, nothing will change with regard to the normally open power relay 192, the latching relay 212, or the first solenoid 154. Therefore, the first trap door 142 will remain closed. However, the circuit to the normally closed power relay 196 will be opened allowing it to move to its deenergized position, i.e., closed. When closed, the power relay 196 completes the circuit to the latching relay 220 which, in turn, completes the circuit to the second solenoid 156 to energize it and thus open the second trap door 146 for an adjustably predetermined length of time. The particular golf ball that was tested and found to have medium compression rating which triggered this "medium" operational mode will fall into the chute 130 and will exit therefrom through the second outlet opening 138. After that particular golf ball has exited the chute 130, the second trap door 146 will be returned to its normally closed position as a result of the lapsing of the time delay of the latching relay 220.

The third operational mode, which is herein referred to as the "hard" golf ball mode, occurs when the golf ball being tested has a compression rating which is high enough to move the pivot contact 178 of the sensing means 18 into engagement with the contact 182. In other words, the switch 100 (FIG. 5) will be opened and the switch 98 will be closed. Opening of the switch 100 will, as described above with reference to the medium operational mode, deenergize the normally closed power relay 196, energize the latching relay 220 and the second solenoid 156, thus opening the second trap door 146. Closing of the switch 98 will energize the normally open power relay 192 so that it will complete the circuit to the first latching relay 212 to energize that relay 212 to its closed position so that it will, in turn, energize the first solenoid 154 and thereby open the first trap door 142. From this, it will be seen that in this "hard" operational mode, both of the trap doors 142 and 146 will be opened for predetermined times in accordance with the time delay adjustment settings of their respective ones of the latching relays 212 and 220. Since the first trap door 142 is upstream of the second trap door 146, the particular golf ball which triggered the "hard" operational mode will exit the chute 130 through the first outlet opening 136 and never reach the second outlet opening 138. When the "hard" golf ball has exited the chute 130, both of the trap doors 142 and 146 will be closed due to lapsing of the adjustable time delays of their respective latching relays 212 and 220.

While the principles of the invention have now been made clear in the illustrated embodiments, there will be immediately obvious to those skilled in the art, many modifications of structure, arrangements, proportions, the elements, materials, and components used in the practice of the invention, and otherwise, which are particularly adapted for specific environments and operation requirements without departing from those principles. The appended claims are therefore intended to cover and embrace any such modifications within the limits only of the true spirit and scope of the invention.

What I claim is:

1. An apparatus for testing the compressibility of a golf ball comprising:
    (a) drive means for defining at least a portion of one side of a golf ball movement path and for driving the golf ball to be tested through at least that portion of the golf ball movement path;
    (b) lever means in spaced relationship with said drive means and including a load arm having a bearing surface which defines the opposite side of the golf ball movement path, said lever means further including a fulcrum means about which it is pivotably movable toward and away from said drive means;

(c) biasing means in engagement with said lever means for yieldably biasing said lever toward said drive means;

(d) stop means for limiting the biased movement of said lever means toward said drive means to form a restricted gap in the golf ball movement path which is smaller than the diameter of the golf ball to be tested so that upon driving of the golf ball through the restricted gap said lever means will be deflectingly moved away from said drive means an amount indicative of the compressibility of the golf ball being tested; and (e) sensing means in engagement with said lever means for detecting and providing indications of the amount of deflected movement of said lever means when the golf ball to be tested is driven through the restricted gap defined by said drive means and said lever means.

2. An apparatus as claimed in claim 1 wherein said drive means is a variable speed device for driving the golf ball to be tested at adjustably variable speeds.

3. An apparatus as claimed in claim 1 wherein said drive means comprises:

(a) a cylindrical drum having a peripheral surface for engaging the golf ball to be tested and driving it through the restricted gap defined by said drive means and said lever means; and (b) a variable speed motor coupled for rotational driving of said cylindrical drum.

4. An apparatus as claimed in claim 3 wherein the peripheral surface of said cylindrical drum has a high-friction finish for gripping of the golf ball to be tested.

5. An apparatus as claimed in claim 1 wherein said bearing surface of said load arm has a high-friction finish for gripping of the golf ball to be tested.

6. An apparatus as claimed in claim 1 wherein said lever means further comprises:

(a) said load arm extending in one direction from said fulcrum means; and (b) a movement transmitting arm integral with said load arm and extending in a different direction from said fulcrum means and disposed for engagement by said sensing means.

7. An apparatus as claimed in claim 6 wherein said bearing surface of said load arm is formed with a flat thereon which is in spaced alignment with said drive means to provide the restricted gap in the golf ball movement path therebetween.

8. An apparatus as claimed in claim 6 wherein said load arm and said movement transmitting arm are disposed at an approximate right angle with respect to each other to form a bell crank lever.

9. An apparatus as claimed in claim 1 including means for adjusting said biasing means.

10. An apparatus as claimed in claim 1 including means for adjusting said stop means to allow the size of the restricted gap defined by said drive means and said lever means to be changed.

11. An apparatus as claimed in claim 1 wherein said stop means comprises:

(a) an ear on said lever means; and (b) an adjustable stop screw for engaging said ear to limit the biased movement of said lever means toward said drive means.

12. An apparatus as claimed in claim 1 wherein the indication provided by said sensing means includes a visual indication.

13. An apparatus as claimed in claim 1 wherein the indications provided by said sensing means includes a first electrical indication for amounts of deflected movement between a relatively low predetermined value and a relatively higher predetermined value and a second electrical indication for amounts of deflected movement above the relatively higher value.

14. An apparatus as claimed in claim 13 wherein said sensing means includes adjustment means for adjusting the relatively low predetermined value at which the first electrical indication is produced.

15. An apparatus as claimed in claim 13 wherein said sensing means includes adjustment means for adjusting the relatively higher predetermined value at which the second electrical indication is produced.

16. An apparatus as claimed in claim 13 and further comprising:

(a) a control circuit means coupled to receive the first and second electrical indications from said sensing means for producing a first control signal in response to a received first electrical indication and a second control signal in response to a received second electrical indication; and (b) golf ball sorting means for receiving the golf ball to be tested subsequent to the testing thereof and having first, second and third golf ball outlet openings, said golf ball sorting means having means coupled to receive the first and second control signals from said control circuit means for selectively directing the receivable golf ball to said first golf ball outlet opening upon receipt of the second control signal, to said second golf ball outlet opening upon receipt of the first control signal and to said third golf ball opening in the absence of the receipt of the first and the second control signals.

17. An apparatus as claimed in claim 16 wherein said control circuit means comprises:

(a) first means for producing the first control signal for a predetermined length of time upon receipt of the first indication from said sensing means; and (b) second means for producing the second control signal for a predetermined length of time upon receipt of the second indication from said sensing means.

18. An apparatus as claimed in claim 17 wherein said first means includes means for adjusting the predetermined length of time which it produces the first control signal and said second means includes means for adjusting the predetermined length of time which it produces the second control signal.

19. An apparatus as claimed in claim 17 wherein said first and second means are latching relays having adjustable time delays.

20. An apparatus as claimed in claim 16 wherein said golf ball sorting means comprises:

(a) an elongated chute having an inlet end for receiving the golf ball to be tested subsequent to the testing thereof and having an outlet end which forms the third golf ball outlet opening, said chute having the first golf ball outlet opening formed in the floor thereof proximate the inlet end and having the second golf ball outlet opening formed in the floor thereof proximate the outlet end;

(b) a first trap door in the first golf ball outlet opening of said chute and movable to open and close the first golf ball outlet opening;

(c) a first solenoid coupled to said first trap door for holding it in the closed position when said first solenoid is deenergized and for opening said first trap door upon energization, said first solenoid coupled to receive the second control signal from said control circuit means and being energized upon receipt thereof;

(d) a second trap door in the second golf ball outlet opening of said chute and movable to open and close the second golf ball outlet opening; and (e) a second solenoid coupled to said second trap door for holding it in the closed position when said second solenoid is deenergized and for opening said second trap door upon energization, said second solenoid being coupled to receive the first control signal from said control circuit means and being energized upon receipt thereof.

21. An apparatus for testing the compressability of golf balls and sorting them in accordance with predetermined compression ratings, said apparatus comprising:

(a) drive means defining at least a portion of one side of a golf ball movement path and for driving the golf balls to be tested one at a time through at least that portion of the golf ball movement path;

(b) lever means in spaced relationship with said drive means for defining the opposite side of the golf ball movement path, said lever means being movable toward and away from said drive means;

(c) biasing means in engagement with said lever means for yieldably biasing said lever means toward said drive means;

(d) stop means for limiting the biased movement of said lever means toward said drive means to form a restricted gap in the golf ball movement path which is smaller than the diameter of the golf ball to be tested so that upon driving of the golf balls through the restricted gap, said lever means will be deflectingly moved away from said drive means amounts indicative of the compressability of the golf balls being tested;

(e) sensing means in engagement with said lever means for detecting the amounts of the deflected movements of said lever means when the golf balls to be tested are driven one at a time through the restricted gap defined by said drive means and said lever means, said sensing means producing first indications for amounts of deflected lever means movements between a relatively low predetermined value and a relatively higher predetermined value and producing second indications for amounts of deflected lever means movements above the relatively higher value;

(f) a control circuit means coupled to receive the first and second indications from said sensing means for producing first control signals in response to received first indications and for producing second control signals in response to received second indications; and (g) golf ball sorting means for receiving the golf balls to be tested subsequent to the testing thereof and having first, second and third golf ball outlet openings, said golf ball sorting means having means coupled to receive the first and second control signals from said control circuit means for selectively directing the receivable golf balls to said first golf ball outlet opening upon receipt of the second control signal, to said second golf ball outlet opening upon receipt of the first control signal and to said third golf ball outlet opening in the absence of any signals received from said control circuit means.

22. An apparatus as claimed in claim 21 and further comprising a hopper means for containing a supply of golf balls to be tested and delivering those golf balls one at a time to said golf ball movement path defined by said drive means and said means.

23. An apparatus as claimed in claim 21 wherein said drive means is a variable speed device for driving the golf balls to be tested at adjustably variable speeds.

24. An apparatus as claimed in claim 21 wherein said drive means comprises:

(a) a cylindrical drum having a peripheral surface for engaging the golf balls to be tested and driving them one at a time through the restricted gap defined by said drive means and said lever means; and (b) a variable speed motor coupled for rotational driving of said cylindrical drum.

25. An apparatus as claimed in claim 24 wherein the peripheral surface of said cylindrical drum has a high-friction finish for gripping of the golf balls to be tested.

26. An apparatus as claimed in claim 21 wherein said lever means comprises:

(a) fulcrum means about which said lever means is pivotably movable; and (b) a load arm having a bearing surface which defines the opposite side of the golf ball movement path.

27. An apparatus as claimed in claim 26 wherein said bearing surface of said load arm has a high-friction finish for gripping of the golf balls to be tested.

28. An apparatus as claimed in claim 21 wherein said lever means comprises:

(a) a fulcrum means;

(b) a load arm extending from said fulcrum means for pivotable movement thereabout, said load arm having a bearing surface which defines the opposite side of the golf ball movement path; and (c) a movement transmitting arm integral with said load arm and extending in a different direction from said fulcrum means and disposed for engagement by said sensing means.

29. An apparatus as claimed in claim 28 wherein said bearing surface of said load arm is formed with a flat thereon which is in spaced alignment with said drive means to provide the restricted gap in the golf ball movement path therebetween.

30. An apparatus as claimed in claim 28 wherein said load arm and said movement transmitting arm are disposed at an approximate right angle with respect to each other to form a bell crank lever.

31. An apparatus as claimed in claim 21 including means for adjusting said biasing means.

32. An apparatus as claimed in claim 21 including means for adjusting said stop means to allow the size of the restricted gap defined by said drive means and said lever means to be changed.

33. An apparatus as claimed in claim 21 wherein said stop means comprises:

(a) an ear on said lever means; and (b) an adjustable stop screw for engaging said ear to limit the biased movement of said lever means toward said drive means.

34. An apparatus as claimed in claim 21 wherein said sensing means further produces visual indications of the amount of deflected lever arm movements.

35. An apparatus as claimed in claim 21 wherein said sensing means includes adjustment means for adjusting the relatively low predetermined value at which the first indications are produced.

36. An apparatus as claimed in claim 21 wherein said sensing means includes adjustment means for adjusting the relatively higher predetermined value at which the second indications are produced.

37. An apparatus as claimed in claim 21 wherein said control circuit means comprises:
   (a) first means for producing one of the first control signals for a predetermined length of time upon receipt of each of the first indications from said sensing means; and
   (b) second means for producing one of the second control signals for a predetermined length of time upon receipt of each of the second indications from said sensing means.

38. An apparatus as claimed in claim 37 wherein said first means includes means for adjusting the predetermined length of time which it produces the first control signal and said second means includes means for adjusting the predetermined length of time which it produces the second control signal.

39. An apparatus as claimed in claim 37 wherein said first and said second means are latching relays having adjustable time delays.

40. An apparatus as claimed in claim 21 wherein said golf ball sorting means comprises:
   (a) an elongated chute having an inlet end for receiving the golf balls to be tested subsequent to the testing thereof and having an outlet end which forms the third golf ball outlet opening, said chute having the first golf ball outlet opening formed in the floor thereof proximate the inlet end and having the second golf ball outlet opening formed in the floor thereof proximate the outlet end;
   (b) a first trap door in the first golf ball outlet opening of said chute and movable to open and close the first golf ball outlet opening;
   (c) a first solenoid coupled to said first trap door for holding it in the closed position when said first solenoid is deenergized and for opening said first trap door upon energization, said first solenoid coupled to receive the second control signals from said control circuit means and being energized upon receipt thereof;
   (d) a second trap door in the second golf ball outlet opening of said chute and movable to open and close the second golf ball outlet opening; and
   (e) a second solenoid coupled to said second trap door for holding it in the closed position when said second solenoid is deenergized and for opening said second trap door upon energization, said second solenoid being coupled to receive the first control signals from said control circuit means and being energized upon receipt thereof.

* * * * *